US009944966B2

(12) United States Patent
Stadtmüller et al.

(10) Patent No.: US 9,944,966 B2
(45) Date of Patent: Apr. 17, 2018

(54) METHOD FOR PRODUCTION OF SINGLE-STRANDED MACRONUCLEOTIDES

(71) Applicant: Technische Universität Kaiserslautern, Kaiserslautern (DE)

(72) Inventors: Ralf Stadtmüller, Kaiserslautern (DE); Nils Tippkötter, Kaiserslautern (DE); Roland Ulber, Kaiserslautern (DE)

(73) Assignee: Technische Universität Kaiserslautern, Kaiserslautern (DE)

( * ) Notice: Subject to any disclaimer, the term of this patent is extended or adjusted under 35 U.S.C. 154(b) by 0 days.

(21) Appl. No.: 14/196,688

(22) Filed: Mar. 4, 2014

(65) Prior Publication Data

US 2015/0252399 A1 Sep. 10, 2015
US 2017/0145460 A9 May 25, 2017

(30) Foreign Application Priority Data

Mar. 4, 2013 (EP) .................................... 13001069

(51) Int. Cl.
*C12Q 1/68* (2018.01)
*C12P 19/34* (2006.01)
*C12N 15/115* (2010.01)

(52) U.S. Cl.
CPC ............ *C12P 19/34* (2013.01); *C12N 15/115* (2013.01); *C12N 2310/16* (2013.01)

(58) Field of Classification Search
None
See application file for complete search history.

(56) References Cited

U.S. PATENT DOCUMENTS 5,714,320 A 2/1998 Kool
2004/0253270 A1* 12/2004 Meng et al. ............... 424/199.1
2005/0059005 A1* 3/2005 Tuschl et al. ..................... 435/6
2005/0142582 A1 6/2005 Doyle et al.
2011/0033854 A1* 2/2011 Drmanac ................ C12P 19/34 435/6.12
2011/0189776 A1* 8/2011 Terns et al. ................... 435/471

FOREIGN PATENT DOCUMENTS

WO WO0106017 1/2001
WO WO03091406 11/2003
WO WO2005024042 3/2005

OTHER PUBLICATIONS

Instructions for Application Data Sheet (ADS) 37 CFR 1.76, attached, accessed Jul. 29, 2015, available at http://www.uspto.gov/patent/forms/forms-patent-applications-filed-or-after-september-16-2012.*
Childs-Disney et al. (A simple ligation-based method to increase the information density in sequencing reactions used to deconvolute nucleic acid selections, RNA. Feb. 2008; 14(2): 390-394).*
Promega (pGEM®-T and pGEM®-T Easy Vector Systems, attached, Nov. 1998).*
Epicentre (Exonuclease III, *E. coli*, attached, Jun. 2012).*
Simonova et al. (Enhanced cellular binding of concatemeric oligonucleotide complexes, Biochimica et Biophysica Acta (BBA)—Biomembranes, vol. 1758, Issue 3, Mar. 2006, pp. 413-418).*
Won et al. (A New Cloning Method for the Preparation of Long Repetitive Polypeptides without a Sequence Requirement, Macromolecules, 2002, 35 (22), pp. 8281-8287, ePub Sep. 19, 2002).*

* cited by examiner

*Primary Examiner* — Aaron A Priest
(74) *Attorney, Agent, or Firm* — McHale & Slavin, P.A.

(57) ABSTRACT

The invention relates to a method for production of single-stranded macronucleotides by amplifying and ligating an extended monomeric single-stranded target nucleic acid sequence ($target_{ss}$) into a repetitive cluster of double-stranded target nucleic acid sequences ($target_{ds}$), and subsequently cloning the construct into a vector (aptagene vector). The aptagene vector is transformed into host cells for replication of the aptagene and isolated in order to optain single-stranded target sequences ($target_{ss}$). The invention also relates to single-stranded nucleic acids, produced by a method of the invention.

9 Claims, 2 Drawing Sheets

(I) 5′ (SEQ ID NO: 1)

Figure 1:
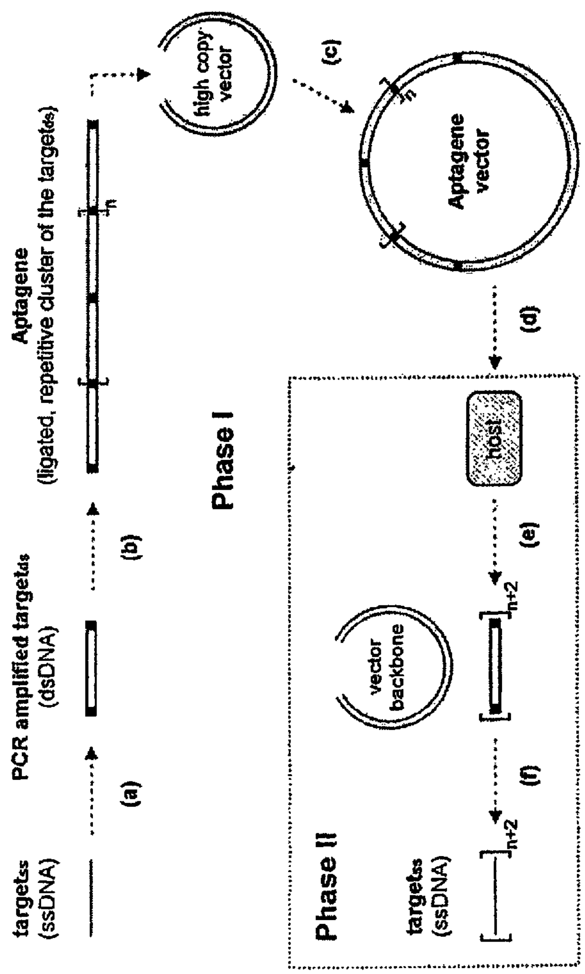

5′ primer site — binding sequence — 3′ primer site ggtattgagggtcgcatcGCTATGGGTGGTCTGGTTGGGATTGGCCCCGGGAGCTGGCagaggagagttagagccatc (II) 5′ (SEQ ID NO: 2)

5′ primer site — binding sequence ggtattgagggtcgcatcGCTATGGGTGGTCTGGTTGGGATTGGCCCCGGGAGCTGGC (III) 5′ (SEQ ID NO: 3)

$n_V$ $rs_C$ $rs_R$ $n_V$ $rs_5$ — linker — binding sequence — $rs_3$ $n_V$ $rs_R$ $rs_C$ $n_V$ CGAGaagcttACGTtatGATTCttgagggtcgcatcGCTATGGGTGGTCTGGTTGGGATTGGCCCCGGGAGCTGGCctgcagTATacgtAAGCTTgtcg (IV) 5′ (SEQ ID NO: 4)

linker — binding sequence — $rs_5$

ATTCttgagggtcgcatcGCTATGGGTGGTCTGGTTGGGATTGGCCCCGGGAGCTGGCctgca

Figure 2

METHOD FOR PRODUCTION OF SINGLE-STRANDED MACRONUCLEOTIDES

CROSS REFERENCE TO RELATED APPLICATIONS

This application claims the benefit of the priority of European Patent Application No. 13001069.7, filed Mar. 4, 2013, the contents of which is incorporated herein by reference.

The present invention relates to a method for production of single-stranded nucleic acids, in particular single-stranded DNA (ssDNA) or single-stranded RNA (ssRNA). The invention further comprises a single-stranded nucleic acid containing at least one desired nucleic acid sequence, obtained by the method according to the present invention.

Isolated single-stranded nucleic acids, in particular single-stranded DNA are routinely used for a number of different industrial and pharmaceutical applications. In modern amplification systems, for instance, ssDNAs are used as primer oligonucleotides in polymerase chain reactions (PCR) or other priming synthesis reactions. They are further used as hybridisation probes, e.g. in micro arrays, or as binding ligands (aptamers) for binding to a specific target site (aptamer). Nucleic acid aptamers are usually engineered through repeated rounds of in-vitro selection or by systematic evolution of ligands applying exponential enrichment (SELEX). Aptamers are able to bind to various molecule targets such as nucleic acids, proteins or small molecules, and whole tissues or cells. Due to their binding capabilities, aptamers are often used as a replacement for antibodies because they produce only little or no immunogenicity in mammalian environments.

One advantage of aptamers is their small molecular weight, resulting in a reduced steric inhibition as compared to heavy antibodies. Furthermore, aptamers allow for renaturation after treatment with solutions of high or low ionic strength, pH or temperature. Aptamers also allow for the selection against cell-toxic compounds and can be used in non-physiological environments.

In view of their industrial and pharmaceutical properties, the production of aptamers, but also other single-stranded DNA or RNA, is a challenge, in particular when it comes to large-scale production. Currently, ssDNA is produced using phosphoramidit chemistry, which is a solid phase synthesis method that generates a single DNA-strand by adding nucleotides on a one by one basis to the steadily growing strand. The efficiency of each coupling step of this method is limited, leading to synthesis errors increasing with the growing length of the desired sequence, e.g. in nearly half of the load of synthesized ssDNA with a desired length of 100 nucleotides. The high error rate, in particular in longer single-stranded nucleic acid molecules, decreases the activity of the molecule and increases the risk of unwanted side effects or adverse reactions, in particular in pharmaceutical applications. Aptamers, produced by using phosphoramidit chemistry, are currently subject of a number of clinical studies that include the treatment of cancer. Therefore, a large-scale production process for single-stranded nucleic acids, resulting in highly qualitative single-stranded products having high sequence integrity is desirable, especially in industrial or pharmaceutical applications.

US 2005/0142582 A1 describes a method for obtaining an aptamer having high affinity to a target molecule. The method comprises the provision of a target molecule with a polyhistidine affinity tag for magnetic beads, binding of the target molecule to these magnetic beats, contacting the target molecules with a library of day-generated potential aptamer sequences to allow binding of aptamer sequences to the target molecule and forming of bead-target-aptamer sequence complexes. The bead-target-aptamer sequence complexes are then separated from the library of non-binding aptamer sequences. The target-bound aptamer sequences are separated from said magnetic beads to form a pool of binding aptamer sequences. The resulting binding aptamer sequences are finally amplified and purified.

The sequence of a single aptamer monomer is usually in the range of 30 to 80 nucleotides. Longer aptamers are desirable because they are able to form more complex tertiary structures and therefore exhibit higher-binding specificity. The need for production methods to produce ssDNA in a range of about 60 to 100 nucleotides or more nucleotides becomes evident, especially when taking into account that a chimer of two or more aptamers is separated by a central sequence (spacer) that avoids steric inhibition during the three-dimensional folding process of the aptamer molecule.

It is therefore an object of the present invention to provide a method for production of single-stranded nucleic acid molecules in a high quality grade and at high quantity.

This object is solved by a method containing the features of claim 1. Preferred embodiments are claimed in the subsequent sub-claims.

The method according to the present invention is based on the replication and amplification of a repetitive cluster of a desired target nucleic acid sequence within a vector. The term "aptagene" as used herein refers to multiple copies of a target sequence, i.e. cluster, within a single nucleic acid molecule. An aptagene may contain any functional or non-functional nucleic acid sequence, including, but not limited to a DNA sequence that comprises control and coding sequences.

All single-stranded nucleic acid sequences as described herein are written from 5' to 3', unless otherwise indicated. The top strand of each double-stranded nucleic acid sequence is written from 5' to 3' and the bottom strand from 3' to 5', unless otherwise indicated.

The term "primer" as used herein refers to an oligonucleotide which is capable of acting as a point of initiation of synthesis when placed under conditions in which primer extension is initiated. Synthesis of a primer extension product that is complementary to a nucleic acid strand is initiated in the presence of the requisite for different nucleoside triphosphates and the DNA polymerase in an appropriate buffer at a suitable temperature.

The method according to the present invention for production of single-stranded nucleic acids, in particular single-stranded DNA or RNA, comprises the steps:

a. provision of a desired single-stranded target nucleic acid sequence ($target_{ss}$), which contains at least one monomer of a desired nucleic acid sequence,
b. extension of the desired nucleic acid sequence by additional functional or non-functional nucleic acid sequences at one or both flanking ends to obtain an extended single-stranded target nucleic acid sequence ($target_{ss}$),
c. amplification of the extended monomeric single-stranded target nucleic acid sequence ($target_{ss}$) into a double-stranded target nucleic acid sequence ($target_{ds}$),
d. ligation of the double-stranded target nucleic acid sequence ($target_{ds}$) to produce repetitive cluster of the double-stranded target nucleic acid sequence (aptagene), e. cloning of the aptagene produced in step d. into a vector (aptagene vector), f. transformation of the aptagene vector into host cells for replication of the aptagene, g. isolation of the aptagene from the host cells and division of the isolated aptagene to multiple copies of the double-stranded target sequence ($target_{ds}$), h. degradation of the double-stranded target sequence ($target_{ss}$) to single-stranded target sequences ($target_{ss}$).

The desired single-stranded target nucleic acid sequence ($target_{ss}$) may be any sequence of interest, including, but not limited to functional nucleic acid sequences, non-functional nucleic acid sequences, genes, ssDNA, ssRNA, artificial nucleic acid molecules, modified nucleic acid molecules and chimeric nucleic acid sequences.

Provision and Extension of a Desired Nucleic Acid Sequence

In a first embodiment, the desired single-stranded target nucleic acid sequence is provided as a monomer, which encodes for at least the desired target nucleic acid sequence (e.g. DNA sequence, RNA sequence). In order to obtain a cluster of a repetitive single-stranded target nucleic acid sequence, i.e. an aptagene, the desired nucleic acid sequence is extended by additional functional or non-functional nucleic acid sequences at the 5'-terminus and/or 3'-terminus, resulting in an extended single-stranded target nucleic acid sequence ($target_{ss}$). Thus, the sequence of each monomer encodes for at least the desired nucleic acid sequence, e.g. the aptamer sequence, extended by one or more different or identical restriction sites or one or more additional functional or non-functional sequences or nucleotides.

Preferably, the desired nucleic acid sequence comprises at least one monomer of a functional aptamer. In an alternative embodiment, the desired nucleic acid sequence contains more than one monomer sequentially arranged to each other, and optionally separated by spacer sequences or functional sequences, e.g. restriction sites. As such the resulting aptagene consists of multiple copies of one or more aptamer sequences. In a preferred embodiment the aptamer sequences (or any other desired nucleic acid sequences) arranged in the aptagene can be the same or different.

The additional functional or non-functional sequences at one or both flanking ends of the desired nucleic acid sequence used for extension of the desired nucleic acid are preferably selected from the group consisting of primer sequences, linker sequences, additional aptamer sequences, spacer sequences, restriction sites, or any combination thereof. For example, the extended sequences can comprise the original primer site (s) of the SELEX process of an aptamer. The addition of a linker sequence permits the later attachment of the resulting single stranded monomer by hybridisation to a complement nucleic acid sequence that may be immobilised to any solid support. For the generation of multifunctional chimeres, the sequence of one or more additional functional sequences (e.g. aptamers) can be utilized. In order to avoid steric inhibitions, a spacer sequence can be inserted between each functional domain of the monomer. The nucleic acid sequences can be added either at the 3'- and/or the 5'-terminus of a monomer or between monomers in the aptagene.

EXAMPLES

The following examples (EX) illustrate possible organisations of a monomer used for unique cloning of an aptagene.

EX.01 5' aptamer

EX.02 5' priming site-aptamer-priming site

EX.03 5' linker-aptamer

EX.04 5' aptamer one-spacer-aptamer two

A monomeric aptamer (EX.01) can be extended by one or more priming sites flanking the aptamer sequence at its 5'-terminus and its 3'-terminus (EX.02). In addition or alternatively, a linker sequence for binding to a target site can be attached to the aptamer (EX.03). Furthermore, two or more aptamers can be separated by spacing sequences (spacer) (EX.04).

Preferably, the desired single stranded nucleic acid sequence is extended at one or both flanking ends by one or more recognition sites for restriction endonucleases. In a preferred embodiment, the extended desired nucleic acid sequence comprises a 5'-flanking restriction site ($rs_5$) with a protruding 5'-strand and a 3'-flanking restriction site ($rs_3$) with a protruding 3'-strand (5' $rs_5$-monomer-$rs_3$) to mediate the ligation of multiples copies of the monomer to form the aptagene and to enable the separation of the aptagene to monomers again in a way that the target ssDNA is resistant during the degradation of its complement strand by exonuclease III.

The inclusion of restriction sites permits the later restriction and ligation of multiple monomers to one large multicopy fragment (aptagene). Furthermore, the restriction sites mediate a separation of each monomer during the isolation and separation process of the aptagene.

Example

EX.05 5' $rs_5$-monomer-$rs_3$

The monomer is flanked at its 5'-terminus by a 5'-flanking restriction site ($rs_5$) and at its 3'-terminus by a 3'-flanking restriction site ($rs_3$), each containing recognition sequences for specific restriction endonuclease that cut the nucleic acid strand. In a further preferred embodiment, one or more protective sequences can be added in order to avoid unwanted cleavage of monomer sequences. It may be important that the 5'-flanking restriction site ($rs_5$) and the 3'-flanking restriction site ($rs_3$) are not part of the sequence of the monomer itself in order to avoid unwanted restriction.

Exonuclease III only degrades duplex DNA from its 3'-hydroxyl-termini of blunt or 3'-recessed termini. By adding additional recognition sites for a restriction endonuclease ($rs_R$), a protruding 3'-terminus is produced, which is resistant (R) to exonuclease III degradation.

In a preferred embodiment, a monomer is flanked by one or more additional recognition sites ($rs_R$) if a separation of aptagene and vector backbone cannot be realised during the preparation process. The $rs_R$ site can be disregarded if separation of the aptagene and vector backbone can be achieved by other means.

The at least one additional recognition site ($rs_R$) at the 5'-terminus and 3'-terminus can also be designed to protect the aptagene after cutting it out from a high copy vector, while the vector backbone is degraded.

Example

EX.06 5' $rs_R$-$rs_5$-monomer-$rs_3$-$rs_R$

In the above example EX.06, the 5'-flanking restriction site ($rs_5$) and the 3'-flanking restriction site ($rs_3$) are flanked by at least one additional recognition site ($rs_R$) at the 5'-terminus and one at the 3'-terminus to generate protruding 3'-strands, which are resistant (R) to exonuclease III degradation, i.e. the two strands will not be recognized as substrate for the enzyme. Therefore, the entire aptagenes is resistant against exonuclease III treatment. Only after separation of the two strands by the enzymes at the recognition sites $rs_5$ and $rs_3$, the target strand (aptamer) is resistant against exonuclease III, whereas the complementary strand is used as a substrate.

In a preferred embodiment, the extended desired nucleic acid sequence 5' $rs_R$-$rs_5$-monomer-$rs_3$-$rs_R$ comprises at least one cloning recognition site ($rs_C$) to enable cloning of the aptagene into a multiplication vector, for example a high copy vector.

Example

EX.07 5' $rs_C$-$rs_R$-$rs_5$-monomer-$rs_3$-$rs_R$-$rs_C$

The construct can have a sequence composition which may vary such as 5' $rs_C$-$rs_R$-$rs_5$-monomer-$rs_3$-$rs_R$-$rs_C$, $rs_R$ $rs_C$-$rs_5$-monomer-$rs_3$-$rs_C$-$rs_R$, 5' $rs_C$-$rs_R$-$rs_5$-monomer-$rs_3$-$rs_C$-$rs_R$ or any other combination of $rs_3$ $rs_C$ $rs_R$ $rs_5$.

The use of unique cloning sites allows for the later ligation of the entire aptagene with its multiple ligated, extended monomers into a high copy vector. Preferably, the recognition site ($rs_C$) is part of the multiple cloning site of the utilized vector. In one preferred embodiment, the cloning recognition site ($rs_C$) produces 3'-resessed termini to ensure that the vector backbone is degraded by exonuclease III treatment, while the $rs_R$-separated aptagene is resistant against such an enzymatic breakdown.

The aptagene template is extended at both sides by a cloning recognition site ($rs_C$) of a restriction endonuclease, which is preferably a DNA restriction endonuclease for the purpose of the present invention. However, any other enzyme, substance or system may be used in the production process according to the present invention in order to allow the later ligation of the aptagene into a high copy vector (e.g. by LIC (ligation independent cloning or TA-cloning).

Further sequences may be used in combination with the additional recognition site ($rs_R$) for specific degradation of the vector backbone during the isolation process. In order to increase the catalytic activity of the restriction endonucleases, the extended desired nucleic acid sequence preferably comprises one or more variable nucleotides ($n_V$) flanking one or more of the recognition sites $rs_C$ and/or $rs_R$. It is preferred that the number of the variable nucleotides is in the range of 0 to 50, preferably 0 to 25, most preferably 0 to 10. In a preferred embodiment n is >1. The choice of the correct nucleotide length depends on the restriction enzyme used, the respective sequence and other reaction conditions. The final length of the template molecule essentially depends on the length of the desired target sequence. These additional variable nucleotides ($n_V$) are preferably used during the construction of the aptagene.

Examples

EX.08 5' $n_V$-$rs_C$-$n_V$-$rs_R$-$n_V$-$rs_5$-monomer-$rs_3$-$n_V$-$rs_R$-$n_V$-$rs_C$-$n_V$ EX.09 5' $n_V$-$rs_C$-$rs_R$-$rs_5$-monomer-$rs_3$-$rs_R$-$rs_C$-$n_V$ The repetitive cluster in the final aptagene vector preferably consists of the monomer itself and at least five additional nucleotides at its 3'-terminus in order to provide resistance against DNA exonuclease III activity. Preferably, the recognition sites for the restriction endonucleases can be part of a linker sequence or the terminus of each nucleotide of the sequence library during the aptamer engineering SELEX process, which allows an aptagene design without any additional variable nucleotides.

The chosen restriction endonuclease depends on the desired target (aptamer) sequence, the sequence of the utilized high copy vector; and other reaction conditions (e.g. temperature, buffer) for each enzyme. In a preferred embodiment, the utilized restriction endonucleases exhibit nearly 100% activity within the same buffer system.

Amplification of $Target_{ss}$ to $Target_{ds}$

The extended single-stranded target nucleic acid sequence ($target_{ss}$) is amplified in order to obtain a double-stranded nucleic acid sequence ($target_{ds}$). Preferably, a polymerase chain reaction (PCR) is used for this purpose. However, any other amplification method suitable for replicating nucleic acids may be feasible in the utilization of the present invention. The template nucleic acid is provided at a minimum amount to perform the amplification reaction.

Endonuclease Restriction

Upon amplification of the single-stranded target nucleic acid sequence ($target_{ss}$) into a double-stranded target nucleic acid sequence ($target_{ds}$), the amplicons are preferably restricted by three different modes (I-III) to produce different restriction products 5' *$rs_5$-monomer-$rs_3$* (mode I), 5'-$rs_5$-monomer-$rs_3$* (mode II) and 5' *$rs_5$-monomer-$rs_3$- (mode III), each optionally being flanked by one or more additional $rs_C$ and/or $rs_R$ recognition sites and/or $n_V$ nucleotides at the non-restricted terminus. The (*) marks that the recognition site has been restricted by a restriction enzyme.

Mode I comprises the amplicon using the respectively chosen restriction endonucleases for the restriction sites $rs_5$ and $rs_3$. The resulting restriction product is later used for the ligation of the repetitive multiple copies of the aptagene. Two additional restriction products are required (mode II and mode III) to clone the aptagene into a high copy vector. In mode II, the setup contains a second portion of the amplified amplicon together with the restriction endonuclease for the restriction site $rs_3$. The restriction products contain the 5'-terminus at the monomer of the entire aptagene. In mode III, a further part of the amplified amplicon is incubated with the respective restriction endonuclease for the restriction site $rs_5$, resulting in a 3'-terminus monomer of the aptagene.

Examples

Mode I

EX.09 5' $n_V$-$rs_C$-$rs_R$ $rs_5$-monomer-$rs_3$-$rs_R$-$rs_C$-$n_V$

EX.10 5' *$rs_5$-monomer-$rs_3$*

Mode II

EX.11 5' $n_V$-$rs_C$-$rs_R$-$rs_5$-monomer-$rs_3$*

Mode III

EX.12 5' *$rs_5$-monomer-$rs_3$-$rs_R$-$rs_C$-$n_V$

Explanations:

The "*" indicates that the recognition site has been cut.

Mode I: A part of the amplicon is cut at its ends with restriction endonuclease(s) specific for the restriction sites $rs_5$ and $rs_3$, resulting in products that can ligate to multiple repeats (EX. 10).

Mode II: A second portion of the amplicon is treated with the restriction endonuclease(s) for the site $rs_3$ leading to a product (EX. 11) that can be ligated to a $rs_3$ cut end of the products of mode I.

Mode III: A third part of the amplicon is cut by the restriction endonuclease for the site $rs_5$ leading to a product (EX. 12) that can be ligated to a $rs_5$ cut terminus of the products of mode I.

Ligation of Restriction Products

After endonuclease cleavage, the restriction products of the amplified amplicon are enzymatically ligated by incubation with a suitable DNA ligase in an appropriate buffer. In a preferred embodiment, the ligation step comprises the mixing of an excess amount of the restriction products of mode I over the restriction products of mode II and an excess amount of the restriction products of mode I over the restriction products of mode III. A high amount of the restriction products of mode I over a smaller amount of the $rs_3$-treated fragments of mode II ensures that the fragments of mode I have a greater capability to ligate multiple times before a terminal fragment of restriction mode I limits the growth at one terminus. Preferably, the same setup is used for the restriction products of mode I and mode III.

After an evaluated period, both ligation reactions are mixed and an additional portion of the restriction products of mode I is supplemented. The reaction leads to the composition of a large double-stranded nucleic acid sequence (e.g. dsDNA) made of multiple repeats of the products of mode I, flanked by one fragment of mode II at the 5'-terminus and by one fragment of mode III at the 3'-terminus. This construct is called the "aptagene".

Example

EX.13 5' $n_V$-$rs_C$-$rs_R$-$rs_5$-monomer-[$rs_3$-monomer$_C$-$rs_5$-monomer]$_n$-$rs_3$-monomer-$rs_5$-$rs_R$-$rs_C$-$n_V$ The ligated aptagene is the result of a stepwise ligation of the products of the three restriction modes I-III mentioned above.

The aptagene differs at its 5'-terminus and its 3'-terminus by the variable sequences $n_V$. The 5'-terminus and the 3'-terminus of each monomer result in an enrichment of only the desired ligation products in the amplification reaction (PCR). For this purpose, specific terminal binding primers and a proof-reading polymerase are utilized.

The PCR products can be separated by conventional methods and means, e.g. by agarose gel electrophoresis to re-isolate the products of an appropriate size. The isolated aptagene can be directly ligated into a high copy vector, which then will be transformed into a host cell. The transformation efficiency depends on the size of the vector used, the transformation technique and the host microorganism.

Cloning of the Aptagene Vector

The prepared aptagene and preferably a high copy vector are restricted with a suitable endonuclease at the restriction site(s) $rs_C$ (EX. 14 and EX. 15). The restriction products are subsequently ligated by incubation with a DNA ligase.

Even every other suitable technique to clone the aptagene into the vector of choice, e.g. ligation independent cloning, is possible and may be utilized in the present invention.

Examples

EX.14 5' *$rs_C$-$rs_R$-$rs_5$-monomer-[$rs_3$-monomer$_C$-$rs_5$-monomer]$_n$-$rs_3$-monomer-$rs_5$-$rs_R$-$rs_C$*

EX.15 5' *$rs_C$-vector-$rs_C$*

EX.16 vector-$rs_C$-$rs_R$-$rs_5$-monomer-[$rs_3$-monomer$_C$-$rs_5$-monome]$_n$-$rs_3$-monomer-$rs_5$-$rs_R$-$rs_C$-vector Any high copy vector can be utilized in the present invention. A preferred vector contains an origin of replication that ensures a high copy number, e.g. the pUC origin, an selection marker to select only positive clones, e.g. an antibiotic resistance or a metabolic feature, a suitable (multiple) cloning site or any other sequence-motive that enables to clone the aptagene into the vector, a size that is at least the half of the aptagene or less and therefore ensures a high transformation efficiency even in the case of a large aptagene, e.g. because of a long target sequence or a high copy number of the monomer within the aptagene.

Preferably, the utilized vector is a high copy vector selected from the group consisting of pUC18, pUC19, pSMART HCAamp, pSMART HCKan, pBluescript, pGEM-T, pGEM-T easy, pDrive Cloning or derivatives thereof. Preferably, the utilized vector comprises at least half of the size of the aptagene or less in order to obtain high transformation efficiency. Any suitable method can be used for the subsequent transformation of the ligated aptagene vector into the host cell.

Any prokaryotic or eukaryotic host cell that is able to replicate the target sequences of the present invention can be utilized in the present invention.

Preferred host cells are commercial available derivatives of *Escherichia coli* K12 as these strains are well characterized in their genotype and phenotype and are generally regarded as safe. The strains should ensure a high transformation efficiency even in the case of large vectors, a fermentation to high cell density, a preparation of high quality vector DNA, a deficiency for the enzymes that catalyses the genetic recombination, a deficiency for the enzymatic activities of endonucleases and at least a small amount of toxic compounds, as for instance the *Escherichia coli* NEB-10 beta.

Preferred host cells are selected from the group consisting of *Escherichia coli* such as NovaBlue, NEB-5 alpha, NEB-10 beta, DH5 alpha, DH10B, JM109, Endura, SURE.

In a preferred embodiment, the vector backbone permits the replication of the aptagene in bacteria, preferably in *Escherichia coli*, and facilitates the fermentation of high cell densities at short cultivation periods. Preferably, electroporation is used for transformation of the cells, which provides high transformation efficiency.

Following transformation of the aptagene vector into the host cells, the recombinant clone harbouring the aptagene vector is cultivated under appropriate conditions to allow in-vivo replication of the aptagene.

Preferably, the vector backbone enables for the selection of only recombinant clones, for example by an antibiotic resistance or a metabolic feature. Selected clones are singularized, for example by using plating techniques. The ligation success is then verified, preferably by means of plasmid preparation, followed by a restriction analysis or sequencing. At this stage, the singular cloning of the aptagene is accomplished.

The aptagene vector is prepared by standard methodology, e.g. by precipitation of vector DNA from a cell lysate after extraction of the cell protein and the genomic DNA by extraction.

The separation of the aptagene preferably comprises the restriction of the aptagene vector at the cloning recognition sites ($rs_C$) and/or at the restriction recognition sites ($rs_R$). In an alternative embodiment, the preparative isolation of the aptagene, e.g. by a preparative gel electrophoresis, is replaced by an enzymatic degradation of the vector backbone. The produced aptagene vector DNA is treated with a restriction endonuclease which is specific for the restriction site $rs_R$ under the chosen reaction conditions. This results in a dsDNA aptagene that is separated from the vector backbone and is resistant to degradation by DNA exonuclease III, as it exhibits protruding 3'-termini on both strands. In a subsequent step, the restriction endonuclease for the restriction site $rs_C$ or any other restriction endonuclease which does not cleave the aptagene, but only the vector backbone, producing 3'-terminal recessed ends, is supplied. As a result, the vector backbone will be degraded by the addition of exonuclease III, while the aptagene is protected. Finally, the DNA exonuclease RecJ is added, which degrades the ssDNA that remains from the degradation process of the vector by exonuclease III. When heating the reaction for about 20 minutes at 70° C., both exonucleases will be inactivated.

Division of the Aptagene and Conversion to Single-Stranded Nucleic Acid Monomers Preferably, the division of the aptagene to singular monomers comprises the restriction of the aptagene at the 5' restriction sites ($rs_5$) and 3' restriction sites ($rs_3$) followed by degradation of the protruding single-stranded 3' termini by exonuclease treatment. The aptagene is treated with the restriction endonucleases specific for the restriction sites $rs_5$ and $rs_3$, resulting in double-stranded nucleic acid molecules made of monomers with a protruding terminus at both ends (EX. 11).

The complement monomer strand ($monomer_c$) exhibits recessed ends at both of its termini making it the only substrate for the degradation of the DNA exonuclease III in the following step (EX. 17). The exonuclease III binds to the recessed 3'-terminus of each restricted dsDNA molecule and specifically degrades only the monomer, strand by releasing the corresponding nucleotides.

Examples

EX.10 5' *$rs_5$-monomer-$rs_3$*
EX.17 5' nnnnn-monomer-nnnnn
3' n-$monomer_C$-n
EX.18 5' nnnnn-monomer-nnnnn
EX.19 5' monomer-linker The aptagene is divided into singular monomers (EX.10). The entire aptagene is restricted to multiple copies of short dsDNA fragments made of the monomer and the complemented $monomer_c$ (EX.17). "n" represents any one of the nucleotides A, T, C or G, including their analogs and modified nucleotides thereof. The dsDNA molecule contains a terminal protruding monomer strand and a terminal recessed $monomer_C$ strand (EX.18)

The number of additional nucleotides "n" on both termini depends on the chosen restriction endonuclease for the sites $rs_5$ and $rs_3$, and may vary from 0 to 5 n on the 5'-terminus, whereas n>1, preferably n=5 or more on the 3'-terminus is recommended as this number ensures a resistance against degradation of the 3'-termini by exonuclease III treatment. One example of a final product is shown in EX.19. In this embodiment the monomeric target sequence is attached to a linker sequence. However, as mentioned above, any other or no additional sequences may be attached to the monomer sequence.

The obtained product can be purified from the enzymes, mononucleotides and buffer by standard methods, e.g. by phenol/chloroform extraction followed by alcohol precipitation, or affinity chromatography. The final product in all cases is the initially chosen single-stranded nucleic acid (e.g. ssDNA) at large quantity and high sequence integrity, even if the sequences are longer than 100 nucleotides (n>100) or even longer than 250 nucleotides (n>250).

The aptagene technology defines a novel approach in the synthesis of high quality single-stranded nucleic acids such as DNA or RNA, containing 20, 30, 60, 80, 100 or more nucleotides. The method of the present invention is in particular suitable for long nucleic acids strands comprising 100, 150, 250 or more nucleotides. The method of the invention results in a high sequence accuracy and a large production scale that has not been achievable with reasonable effort by conventional methods.

In a preferred embodiment the crafting of already selected functional ssDNAs, e.g. aptamers, can be handled in various ways:

(i) Transferring the aptagene vector to a special host that lacks components of its DNA repair system, e.g. *E. coli* XL-1 red, leads to alterations in the originally cloned aptamer sequence. The rate of mutations depends on the cultivation time and the individual genotype of the host so that the number of alterations can be approximately regulated. As spontaneous mutations occur within the multiple monomers of the aptagene, e.g. enhanced by UV-light, that will not be repaired, a downstream process of this altered aptagene leads to multiple new species of the previously cloned aptamer sequence. These new aptamer species can further be investigated in terms of e.g. lower dissociation constants or binding of their selected target under changed conditions.

(ii) Combining different aptamers during the aptagene design by amplifying various aptamers with the same sites for $rs_5$ and also $rs_3$, and transferring the corresponding mixed aptagene vector to a host that codes the genotype for a recombinase activity chimeres of the previously separately arranged aptamers.

(iii) If different aptagene vectors are already made, the recombination of different aptamers can be achieved by transferring both aptagene vectors in the same host harbouring a recombinase activity.

The present invention will be further illustrated in the accompanying Figures.

FIG. 1 demonstrates the aptagene technology for the production of single-stranded DNA even of large size, maximum sequence integrity and high production. The methodology can be separated in two phases, consisting of a unique cloning step of the aptagene in phase I and a regular production scheme in phase II. Phase I. The unique cloning of an aptagene containing a desired target sequence: (a) The desired target sequence is amplified with specific terminal flanking nucleotides by PCR. (b) These sites are used to ligate multiple PCR products to a repetitive cluster—the aptagene—with more than 100 copies of the target sequence. (c) In the next step, the aptagene is cloned into a high copy vector which forms the 'aptagene vector'. (d) An appropriate microorganism acts as a host and replicates the aptagene vector up to 700 times per cell while being fermented up to a cell density of about $10^{10}$ cells per milliliter. Phase II. The regular production scheme of the specific target sequence: (e). The cells are lysed, the aptagene vector DNA is prepared and divided into the vector backbone and multiple copies of the double-stranded $target_{ds}$ sequence. (f) In a final step, the specific treatment with DNA restriction endonucleases and DNA exonuclease degrades the unwanted complement strands and delivers the single stranded $target_{ss}$ sequence in a high grade. The product can then be purified by phenol/chloroform extraction/precipitation, or other methods, e.g. HPLC or IEX.

FIG. 2 describes an aptagene design for the hexahistidine binding aptamer 6h7. The upper and lower characters indicate nucleic acid sequences with different functions. (I, SEQ ID NO: 1) The sequence of the aptamer 6h7 with the flanking 5'- and 3'-terminal primer sites, which are used in the originally described sequence in the SELEX process. (II, SEQ ID NO: 2) The sequence represents the origin for the aptagene synthesis. The 3'-terminal primer site of the original sequence (I, SEQ ID NO: 1) is not required for the final ssDNA product using the aptagene of the invention. (III, SEQ ID NO: 3) The monomer sequence made of the original binding aptamer sequence and a linker sequence (underlined) for the further attachment of the ssDNA product to a complement oligonucleotide. The linker is arranged as a part of the original 5'primer site (II, SEQ ID NO: 2) and the site $rs_5$. The monomer is further expanded by the sites $rs_3$, $rs_R$, $rs_C$, and the nucleotides $n_V$ that ensures maximum activity of the chosen restriction enzymes during the cloning and downstream process. (IV, SEQ ID NO: 4) The final ssDNA product of the processed aptagene design [II, SEQ ID NO: 2). The binding sequence can be immobilized by the 5'-terminal linker sequence that is close to the original 5' primer site of the aptamer and should not interfere with the functional properties of the aptamer.

a. providing a single-stranded nucleic acid sequence which comprises at least one monomer of an aptamer and which contains a desired target sequence, b. extension of the single-stranded nucleic acid sequence which comprises the at least one monomer of an aptamer by adding additional nucleic acid sequences or nucleotides at both flanking ends of the 5' terminus and 3' terminus to obtain an extended single-stranded target nucleic acid sequence, wherein the extended nucleic acid sequence comprises a 5'-flanking restriction site ($rs_5$) with a single stranded overhang at the 5'-strand and a 3'-flanking restriction site ($rs_3$) with a single stranded overhang at the 3'-strand, thereby forming a nucleic acid sequence of 5' $rs_5$-monomer $rs_3$, and wherein the extended nucleic acid sequence 5' $rs_5$-monomer-$rs_3$ is flanked by at least one additional recognition site ($rs_R$) at the 5'-terminus and 3'-terminus to generate a single stranded overhang at the 3'-strand which is resistant to exonuclease III degradation, thereby forming a nucleic acid sequence of 5' $rs_R$-$rs_5$-monomer-$rs_3$-$rs_R$,

The invention claimed is:

1. A method for production of single-stranded nucleic acids, comprising the steps:

c. amplification of the extended single-stranded target nucleic acid sequence into multiple double-stranded target nucleic acid sequences, wherein after amplification of the single-stranded target nucleic acid sequence into a double-stranded target nucleic acid sequence, amplicons are restricted by mode I to produce restriction products 5' *$rs_5$-monomer-$rs_3$*, mode II to produce 5'-$rs_5$-monomer-$rs_3$* and mode III to produce 5' *$rs_5$-monomer-$rs_3$-, each optionally being flanked by one or more additional $rs_C$ and/or $rs_R$ recognition sites and/or nucleotides at the non-restricted terminus, wherein the (*) marks that the recognition site has been restricted, d. ligation of the multiple double-stranded target nucleic acid sequences to produce an aptagene comprising a repetitive cluster of the double-stranded target nucleic acid sequence, e. cloning of the aptagene produced in step d. into an aptagene vector, f. transformation of the aptagene vector into host cells for replication of the aptagene, g. isolation of the aptagene from the host cells to obtain multiple copies of the double-stranded target sequence, h. division of the aptagene to singular monomers and degradation of the double-stranded target sequence to form multiple single-stranded target sequences which comprises the at least one monomer of an aptamer described in step a by restriction of the aptagene at the 5' restriction sites ($rs_5$) and 3' restriction sites ($rs_3$) followed by degradation of strands with recessed 3'-termini by exonuclease III treatment.

2. The method according to claim 1, wherein the additional nucleic acid sequences or nucleotides at both flanking ends for extension of the single-stranded nucleic acid sequence which comprises at least one monomer of an aptamer described in step b. are selected from the group consisting of primer sequences, linker sequences, additional aptamer sequences, spacer sequences, restriction sites, or a combination thereof.

3. The method of claim 1, wherein the extended nucleic acid sequence aptamer 5 $rs_R$-$rs_5$-monomer $rs_3$-$rs_R$ comprises at least a cloning recognition site ($rs_c$) to enable cloning of the aptagene into the vector of step e, thereby forming a nucleic acid sequence of 5 $rs_c$-$rs_R$-$rs_5$ monomer-$rs_3$-$rs_R$-$rs_c$.

4. The method of claim 3, wherein the extended nucleic acid sequence comprises one or more variable nucleotides ($n_V$) flanking one or more of the recognition sites $rs_C$ and/or $rs_R$.

5. The method of claim 1, wherein the ligation of step d comprises mixing of an excess amount of the restriction products of mode I over the restriction products of mode II and an excess amount of the restriction products of mode 1 over the restriction products of mode III.

6. The method of claim 1, wherein the aptagene vector is transferred into a host that lacks components of its DNA repair system, resulting in alterations in the originally cloned aptamer sequence.

7. The method of claim 3, wherein separation of the aptagene comprises restriction of the aptagene vector at the cloning recognition sites ($rs_C$) and/or at restriction recognition sites ($rs_R$).

8. The method according to claim 1, wherein the resulting single-stranded target sequences comprises more than 60 nucleotides.

9. The method of claim 6, wherein said host that lacks components of its DNA repair system is *E. coli* XL-1 red.

* * * * *

SEQUENCE LISTING

```
<160> NUMBER OF SEQ ID NOS: 4

<210> SEQ ID NO 1
<211> LENGTH: 78
<212> TYPE: DNA
<213> ORGANISM: Homo sapiens

<400> SEQUENCE: 1

ggtattgagg gtcgcatcgc tatgggtggt ctggttggga ttggccccgg gagctggcag     60

aggagagtta gagccatc                                                   78


<210> SEQ ID NO 2
<211> LENGTH: 58
<212> TYPE: DNA
<213> ORGANISM: Homo sapiens

<400> SEQUENCE: 2

ggtattgagg gtcgcatcgc tatgggtggt ctggttggga ttggccccgg gagctggc       58


<210> SEQ ID NO 3
<211> LENGTH: 99
<212> TYPE: DNA
<213> ORGANISM: Homo sapiens

<400> SEQUENCE: 3

cgagaagctt acgttatgat tcttgagggt cgcatcgcta tgggtggtct ggttgggatt     60

ggccccggga gctggcctgc agtatacgta agcttgtcg                            99


<210> SEQ ID NO 4
<211> LENGTH: 63
<212> TYPE: DNA
<213> ORGANISM: Homo sapiens

<400> SEQUENCE: 4

attcttgagg gtcgcatcgc tatgggtggt ctggttggga ttggccccgg gagctggcct     60

gca                                                                   63
```